US009113787B2

(12) United States Patent
Maeda et al.

(10) Patent No.: US 9,113,787 B2
(45) Date of Patent: Aug. 25, 2015

(54) ELECTRONIC ENDOSCOPE SYSTEM

(75) Inventors: Kiyohiro Maeda, Kanagawa (JP);
Takayuki Iida, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 445 days.

(21) Appl. No.: 13/283,396

(22) Filed: Oct. 27, 2011

(65) Prior Publication Data
US 2012/0176486 A1 Jul. 12, 2012

(30) Foreign Application Priority Data
Jan. 11, 2011 (JP) ................................. 2011-003110

(51) Int. Cl.
*A61B 5/00* (2006.01)
*A61B 1/00* (2006.01)
*A61B 1/06* (2006.01)
*A61B 5/1455* (2006.01)
(Continued)

(52) U.S. Cl.
CPC ............. *A61B 5/0084* (2013.01); *A61B 1/0005* (2013.01); *A61B 1/00009* (2013.01); *A61B 1/00186* (2013.01); *A61B 1/0638* (2013.01); *A61B 1/0646* (2013.01); *A61B 5/0075* (2013.01); *A61B 5/1459* (2013.01); *A61B 5/14551* (2013.01); *G01J 3/10* (2013.01); *G01J 3/28* (2013.01); *G01J 3/42* (2013.01); *G02B 23/2484* (2013.01); *A61B 5/7232* (2013.01)

(58) Field of Classification Search
CPC ................................ A61B 1/015; A61B 1/126
USPC ........................................................... 348/68
See application file for complete search history.

(56) References Cited

U.S. PATENT DOCUMENTS

2004/0186383 A1 9/2004 Rava et al.
2006/0069306 A1 3/2006 Banik et al.
(Continued)

FOREIGN PATENT DOCUMENTS

EP 2 105 086 A1 9/2009
EP 2 106 738 A1 10/2009
(Continued)

OTHER PUBLICATIONS

European Search Report dated May 29, 2012.
(Continued)

*Primary Examiner* — Jay Patel
*Assistant Examiner* — Frank Huang
(74) *Attorney, Agent, or Firm* — McGinn IP Law Group, Pllc

(57) ABSTRACT

In an endoscope system, rays of different wavelength bands are sequentially projected toward a target site of a test subject, to obtain image signals from the reflected rays. Reflection spectra are calculated from the image signals and subjected to a multi-regression analysis in combination with absorption spectra of those objects which are relevant to the inspection, such as blood or hemoglobin in the target site, and absorption spectra of irrelevant objects other than the relevant objects, such as bile or staining materials. Spectral components of the irrelevant objects in the reflection spectra are determined through the multi-regression analysis, and are eliminated from the reflection spectra, providing second reflection spectra. A couple of images are produced and displayed on the basis of the first reflection spectra from which the spectral components of the irrelevant objects are not eliminated and the second reflection spectra.

19 Claims, 11 Drawing Sheets

(51) Int. Cl.
    *A61B 5/1459* (2006.01)
    *G01J 3/10* (2006.01)
    *G01J 3/28* (2006.01)
    *G01J 3/42* (2006.01)
    *G02B 23/24* (2006.01)

(56) References Cited

U.S. PATENT DOCUMENTS

| | | |
|---|---|---|
| 2007/0213588 A1 | 9/2007 | Morishita et al. |
| 2008/0192246 A1* | 8/2008 | Neiss et al. .................... 356/301 |
| 2009/0036741 A1 | 2/2009 | Igarashi et al. |
| 2009/0306476 A1* | 12/2009 | Banik et al. .................... 600/158 |
| 2010/0198080 A1* | 8/2010 | Liu et al. ........................ 600/477 |
| 2010/0256447 A1 | 10/2010 | Dubi et al. |
| 2011/0069868 A1 | 3/2011 | Tsuruoka |
| 2012/0065948 A1* | 3/2012 | Tan et al. .......................... 703/2 |

FOREIGN PATENT DOCUMENTS

| | | |
|---|---|---|
| EP | 2 359 745 A1 | 8/2011 |
| JP | 2006-181387 A | 7/2006 |
| JP | 2006-187547 | 7/2006 |
| JP | 2006-187547 A | 7/2006 |
| JP | 2006-326153 A | 12/2006 |
| WO | WO 2005/016134 A1 | 2/2005 |
| WO | WO 2007/116663 A1 | 10/2007 |
| WO | WO 2009/145157 A1 | 12/2009 |

OTHER PUBLICATIONS

Notification of Reason(s) for Refusal dated Sep. 18, 2013.
Notification of Reasons for Refusal dated Nov. 16, 2012, with English translation.
European Search Report dated Jan. 2, 2013.

* cited by examiner

| IDENTIFIER | NAME OF OBJECT | ABSORPTION SPECTRUM |
|---|---|---|
| a1 | OXYGENATED HEMOGLOBIN (HbO) | |
| a2 | REDUCED HEMOGLOBIN (Hb) | |
| a3 | BLOOD | |
| a4 | PLASMA | |
| a5 | BILE | |
| a6 | BILIRUBIN | |
| a7 | MELANIN | |
| a8 | MUCIN | |
| a9 | INDIGOCARMINE | |
| a10 | CRYSTAL VIOLET | |
| a11 | IODINE | |
| ⋮ | ⋮ | ⋮ |

| SUBSTANCE NAME | RELEVANT | IRRELEVANT | EXCLUDED |
|---|---|---|---|
| OXYGENATED HEMOGLOBIN (HbO) | ☑ | ☐ | ☐ |
| REDUCED HEMOGLOBIN (Hb) | ☑ | ☐ | ☐ |
| BLOOD | ☑ | ☐ | ☐ |
| PLASMA | ☑ | ☐ | ☐ |
| BILE | ☐ | ☑ | ☐ |
| BILIRUBIN | ☐ | ☑ | ☐ |
| MELANIN | ☐ | ☑ | ☐ |
| MUCIN | ☐ | ☑ | ☐ |
| INDIGOCARMINE | ☐ | ☐ | ☑ |
| CRYSTAL VIOLET | ☐ | ☐ | ☑ |
| IODINE | ☐ | ☐ | ☑ |
| ⋮ | | ⋮ | |

ELECTRONIC ENDOSCOPE SYSTEM

BACKGROUND OF THE INVENTION

1. Field of the Invention

The present invention relates to an endoscope system that projects light in different wavelength bands toward a target site of a test subject to acquire information about relevant objects, or objects of interest, existing in the target site. The present invention relates also to a display method for displaying images obtained by the endoscope system.

2. Description of the Related Art

Various kinds of spectral measurements have been applied to the medical and industrial fields. Endoscopy may be recited as a typical exemplar of the spectral measurement. As well-known in the art, an endoscope is configured to project illumination light from a distal end of a probing portion, which is introduced into a test subject, toward a target site inside the test subject, thereby to capture images of the target site.

Conventionally, a white light source like a xenon lamp or a metal halide lamp has been used as the illuminator of the endoscope. Recently, many methods of capturing images of a target site under illumination light of narrow wavelength bands (narrowband light) are in the spotlight as devices for making it easier to find out pathologies or lesions in the target site. Also such methods have been studied and developed that are intended to acquire information about densities or concentrations of light absorbing components, such as oxygen saturation of blood hemoglobin, or information about depths of blood vessels from the surface of the target site on the basis of image signals obtained under the illumination of narrowband light (see JPA2006-326153 and WO2007/116663).

According to a prior art disclosed in JPA2006-326153, because oxygenated hemoglobin and reduced hemoglobin have the same degree of absorbency to light of 805 nm, a ray of 780 nm (first wavelength) and a ray of 830 nm. (second wavelength) are projected toward a target site, the first and second wavelength being on opposite sides of the isosbestic wavelength of 805 nm. Then, differences in light volume of the reflected light from the target site are calculated between these rays of the first and second wavelengths. As for oxygenated hemoglobin, the difference will be a positive value. When hemoglobin is in an intermediate condition between oxygenated and reduced, the difference will be approximately zero. When hemoglobin is in the reduced condition, the difference will be a negative value. On the basis of the calculated differences, this prior art measures a value corresponding to the transitional oxygen binding rate of red blood cells that are moving in capillary vessels.

In a prior art disclosed in WO2007/116663, blue and green narrowband rays are projected toward a target site, and image signals obtained under these narrowband rays are subjected to a matrix operation such that the color of blood (an example of objects of interest that are relevant to the inspection) is converted into brown, for example, whereas the color of bile (an example of objects of no interest that are irrelevant to the inspection) is converted into magenta, for example. Thus blood or blood vessels and bile are shown in different colors in the captured image, preventing misperceiving bile as blood.

Because oxygen saturation of blood hemoglobin or blood vessel depth is not directly measured as an actual quantitative value but merely estimated from the image signals obtained under the illumination of narrowband light, the estimated value can be adversely affected by irrelevant objects which may exist in the target site but are irrelevant or extraneous for the inspection of relevant objects, i.e. blood or blood vessels in this case. That is, irrelevant objects may lower the adequacy and reliability of the obtained vascular information. The above-mentioned JPA2006-326153 does not disclose any measures for ensuring adequacy and reliability of vascular information against influence of the irrelevant objects.

Along with the demand for eliminating influence of irrelevant objects on the information about relevant objects like blood vessels, it becomes desirable for the operator of the endoscope or the doctor to be able to confirm that influence of the irrelevant objects is certainly eliminated from the obtained information. If the doctor is not sure of the obtained endoscopic information, he or she cannot effectively use the information for diagnosis. The prior art disclosed in WO2007/116663 merely discriminates the bile or object of no concern from the blood or object of concern by coloring them differently from each other. This prior art does not eliminate influence of the irrelevant objects.

SUMMARY OF THE INVENTION

In view of the foregoing, an object of the present invention is to provide an endoscope system that solves the above problems: providing highly-reliable information about relevant objects while ensuring the operator that influence of the irrelevant objects is eliminated from the information.

An endoscope system of the present invention includes an information acquiring device, an eliminating device and a display device. The information acquiring device acquires information about at least a relevant object that exists in a target site of a test subject and is relevant to inspection of the test subject on the basis of the image signal output from an imaging device that captures light reflected from or emitted from the target site while a light projecting device is projecting light toward the target site. The eliminating device eliminates influence of the irrelevant objects other than the relevant object from the information about the relevant object, and the display device graphically displays information about the relevant object. The display device concurrently or time-sequentially displaying the information about the relevant object in a condition before influence of the irrelevant objects is eliminated and in a condition after influence of the irrelevant objects is eliminated.

The relevant object may include blood in blood vessels in the target site or at least a component of the blood. The irrelevant objects may include secretions from the test subject or staining material applied to the test subject.

In an embodiment, the eliminating device eliminates influence of the irrelevant objects by blowing off, rinsing away or sucking out the irrelevant objects from the target site. The eliminating device may include an insufflating or watering function provided in an endoscope.

Preferably, the endoscope system further includes a reflection spectrum obtaining device for obtaining first reflection spectra of the light projected from the light projecting device and reflected from the target site, and a calculating device for calculating spectral components originated from the irrelevant objects within the first reflection spectra through comparison of the first reflection spectra with respective absorption spectra of the relevant and irrelevant objects.

The eliminating device may preferably eliminate the spectral components of the irrelevant objects as calculated by the calculating device from the first reflection spectra, and the information acquiring device may preferably acquire the information about the relevant object on the basis of the first reflection spectra from which the spectral components of the irrelevant objects are not eliminated and second reflection spectra from which the spectral components of the irrelevant objects have been eliminated.

In one embodiment, the endoscope system further includes a memory device for previously storing absorption spectra of the relevant or irrelevant objects, at least one absorption spectrum for each substance.

In another embodiment, the reflection spectrum obtaining device obtains first reflection spectra in a condition where an irrelevant object exists in the target site and second reflection spectra in a condition where the irrelevant object does not exist in the target site, and determines the absorption spectra of the irrelevant object by subtracting the second reflection spectra from the first reflection spectra.

Preferably, the calculating device may carry out a multi-regression analysis using the first reflection spectra as response variables and the absorption spectra of the relevant and irrelevant objects as explanatory variables, and calculates the spectral components of the irrelevant objects by multiplying the absorption spectra of the irrelevant objects with respective weighting coefficients which are determined for each absorption spectrum by the multi-regression analysis.

Preferably the endoscope system may further include an evaluating and deciding device that evaluates the degree of influence of the individual irrelevant object on the first reflection spectra on the basis of the spectral component originated from the irrelevant object, to decide by the degree of influence whether to eliminate the spectral component of the irrelevant object from the first reflection spectra or not.

The evaluating and deciding device may evaluate the degree of influence of the irrelevant objects on the first reflection spectra using either the weighting coefficients determined for the absorption spectra of irrelevant objects by the multi-regression analysis or a statistic value for judging significance of the multi-regression analysis, or both.

The display device may preferably display information as to whether there are any irrelevant objects in the target site, and/or the degree of influence of the irrelevant objects on the first reflection spectra.

Preferably, the endoscope system may further include a sorting device for sorting between relevant and irrelevant objects in advance to the inspection.

In another aspect of the invention, a method of displaying images of a test subject inspected by an endoscope includes the steps of:
  projecting light toward a target site of the test subject;
  capturing light reflected from or emitted from the target site to output an image signal;
  acquiring, on the basis of the image signal, information about at least a relevant object that exists in the target site and is relevant to the inspection;
  eliminating influence of irrelevant objects other than the relevant object from the acquired information; and
  concurrently or sequentially displaying images showing the information about the relevant object before and after having the influence of the irrelevant objects eliminated therefrom.

Another method of displaying images of a test subject inspected by an endoscope may include the steps of:
  projecting light toward a target site of the test subject;
  capturing light reflected from or emitted from the target site to output an image signal;
  acquiring, on the basis of the image signal, information about at least a relevant object that exists in the target site and is relevant to the inspection;
  eliminating irrelevant objects other than the relevant object from the target site; and
  concurrently or sequentially displaying images showing the information about the relevant object acquired before and after the irrelevant objects are eliminated.

According to the present invention, the irrelevant objects are physically eliminated from the target site or virtually eliminated from the graphical information acquired from the target site, and the information about the relevant object is displayed in a condition before the irrelevant objects is eliminated and in a condition after the irrelevant objects is eliminated. Thus the operator of the endoscope system can visually confirm that influence of the irrelevant objects has been eliminated from the information about the relevant object, which will ensure the reliability of the information.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 13 is a diagram showing a sorting list for sorting objects according to their degree of relevancy.

DESCRIPTION OF THE PREFERRED EMBODIMENTS

Figure 1:
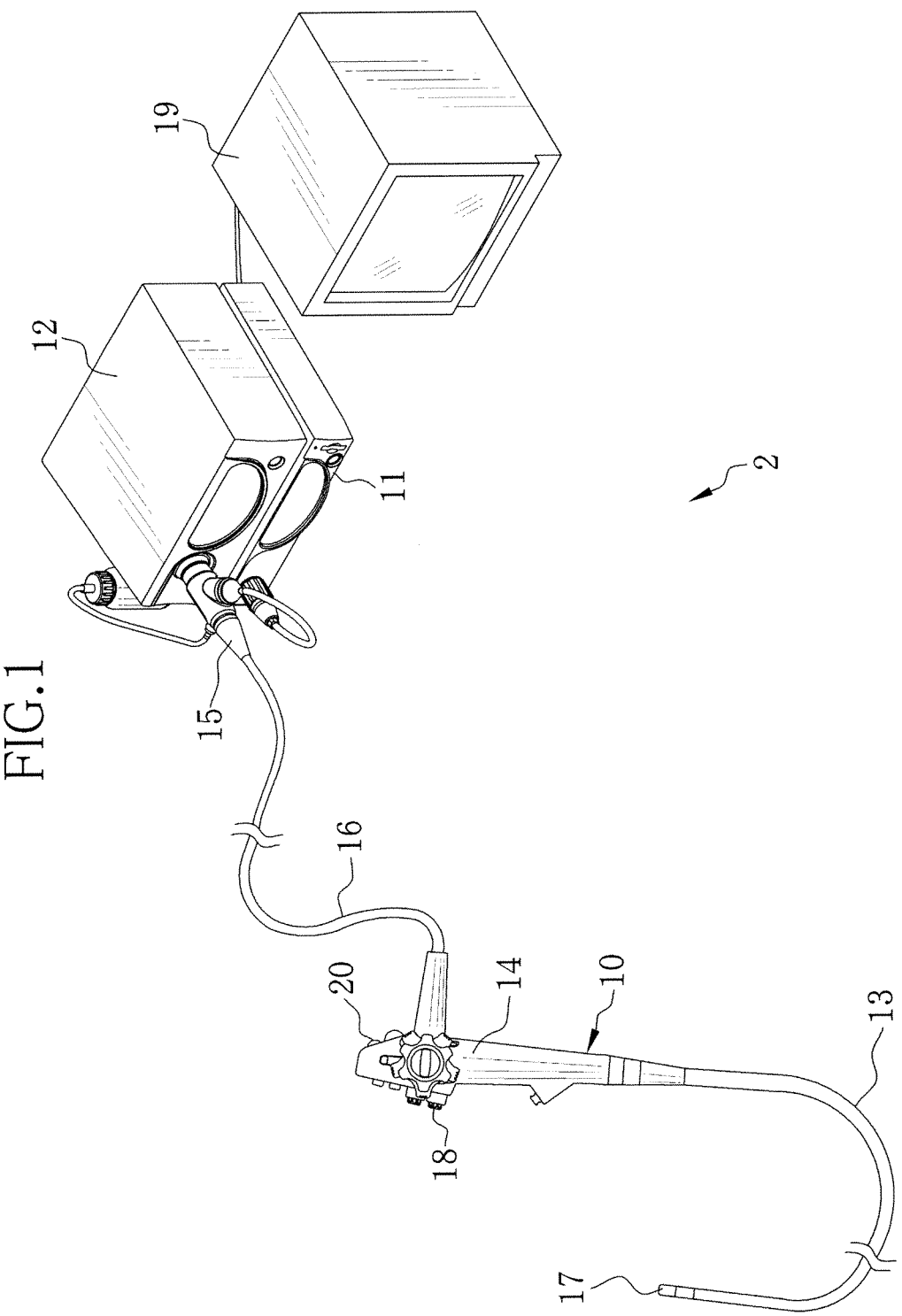
FIG. 1 is a diagram illustrating an outer appearance of an electronic endoscope system.

In FIG. 1, an electronic endoscope system 2 consists of an electronic endoscope 10, a processor unit 11 and a light source unit 12. As well-known in the art, the electronic endoscope 10 has a flexible probing portion 13 to be inserted into body cavities of a test subject or patient, a handling portion 14 coupled to a proximal end of the probing portion 13, a connector 15 to the processor unit 11 and the light source unit 12, and an universal cord 16 interconnecting between the handling portion 14 and the connector 15.

The handling portion 14 is provided with an angle knob for curving the distal end 17 of the probing portion 13 in any directions, a button 18 for causing an insufflating and watering nozzle 33 (see FIG. 2) to eject the air or water, and other operational members including a release button for recording a monitored endoscopic image as a still image frame.

The handling portion 14 is further provided with a tool inlet for inserting a surgical tool like an electric scalpel. The tool inlet is connected to a tool outlet 32 of the distal end 17 (see FIG. 2) through a tool channel along inside the probing portion 13.

The processor unit 11 is electrically connected to the light source unit 12 and controls the overall operation of the electronic endoscope system 2. The processor unit 11 supplies power to the endoscope 10 through the cord 16 and a transmission cable that extends along inside the probing portion 13, to drive a CCD 35 (see FIG. 3) that is mounted in the distal end 17. The processor unit 11 also receives image signals from the CCD 35 via the transmission cable, and processes the image signals to produce image data. The image data is served to display the endoscopic image on a monitor 19 that is connected to the processor unit 11 through a cable.

The electronic endoscope system 2 is provided with an ordinary inspection mode for inspecting a target site of the test subject under the illumination of white light, and a special inspection mode for acquiring specified information about the target site under the illumination of a specific narrowband ray. In the present embodiment, the specified information is information about blood vessels inside the target site. These modes are switchable by operating a mode change-over switch 20 of the handling portion 14. The electronic endoscope system 2 may be automatically set in the ordinary inspection mode as an initial condition immediately after the electronic endoscope system 2 is powered on.

Figure 2:
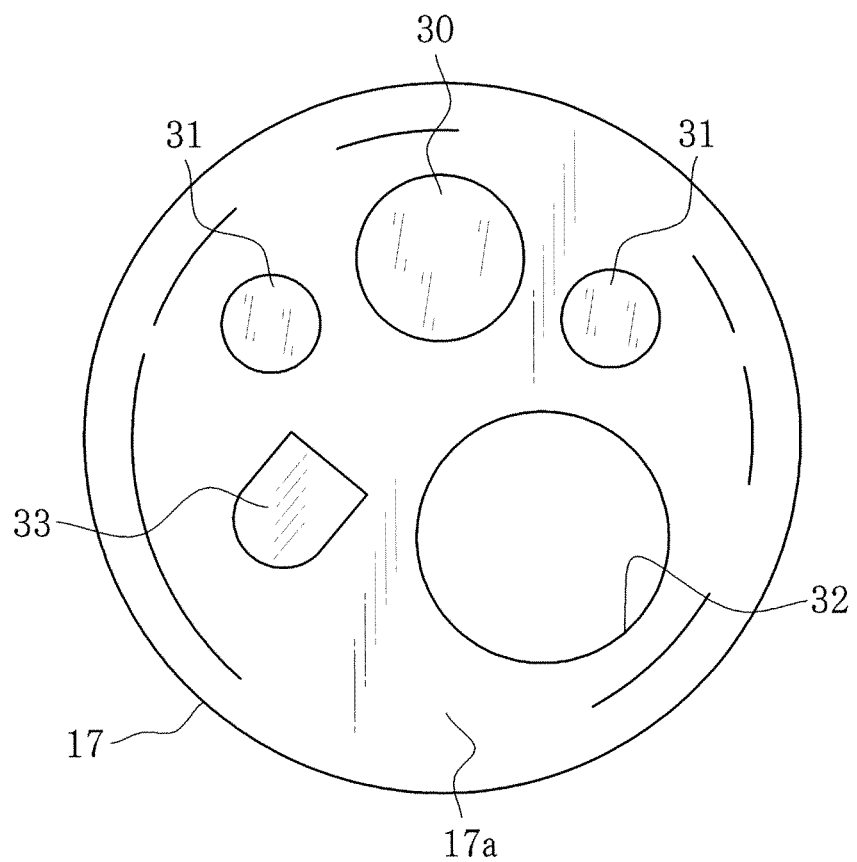
FIG. 2 is a front view of a face of a distal end of an endoscope
Figure 3:
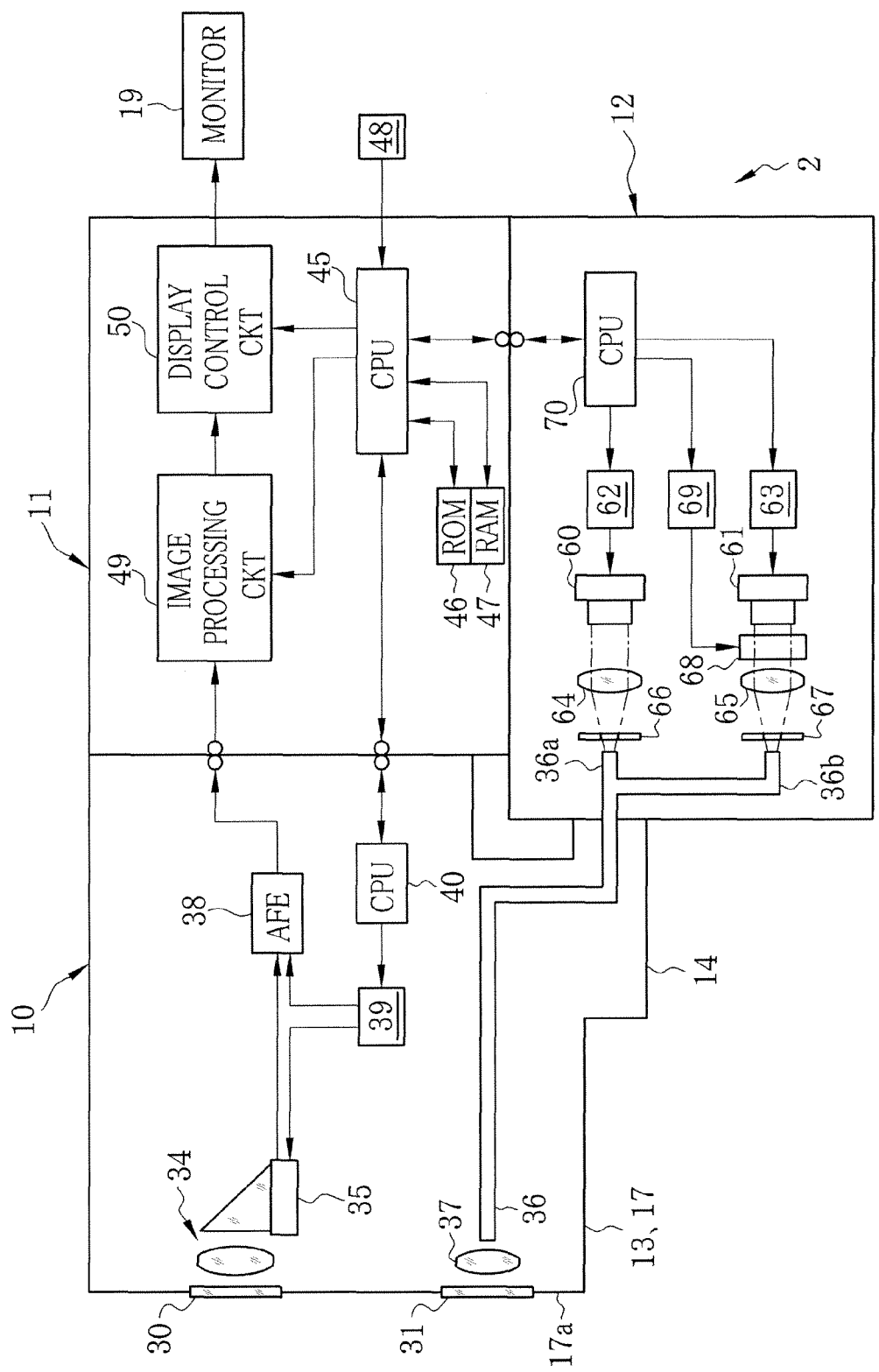
FIG. 3 is a block diagram illustrating the internal structure of the electronic endoscope system.

As shown in FIG. 2, an inspection window 30, a couple of lighting windows 31, the tool outlet 32, and the insufflating and watering nozzle 33 are provided in a face end 17a of the distal end 17. The inspection window 30 is located in one sector of the face end 17a, and the light projection windows 31 are positioned symmetrically on opposite sides of the inspection window 30. As shown in FIG. 3, an objective lens system 34 and the CCD 35 are placed behind the inspection window 30. Illumination light from the light source unit 12, which is conducted through the cord 16, a light guide 36 extending along inside the probing portion 13, and a light projecting lens 37, is projected from the light projection window 31 toward the target site.

Figure 4:
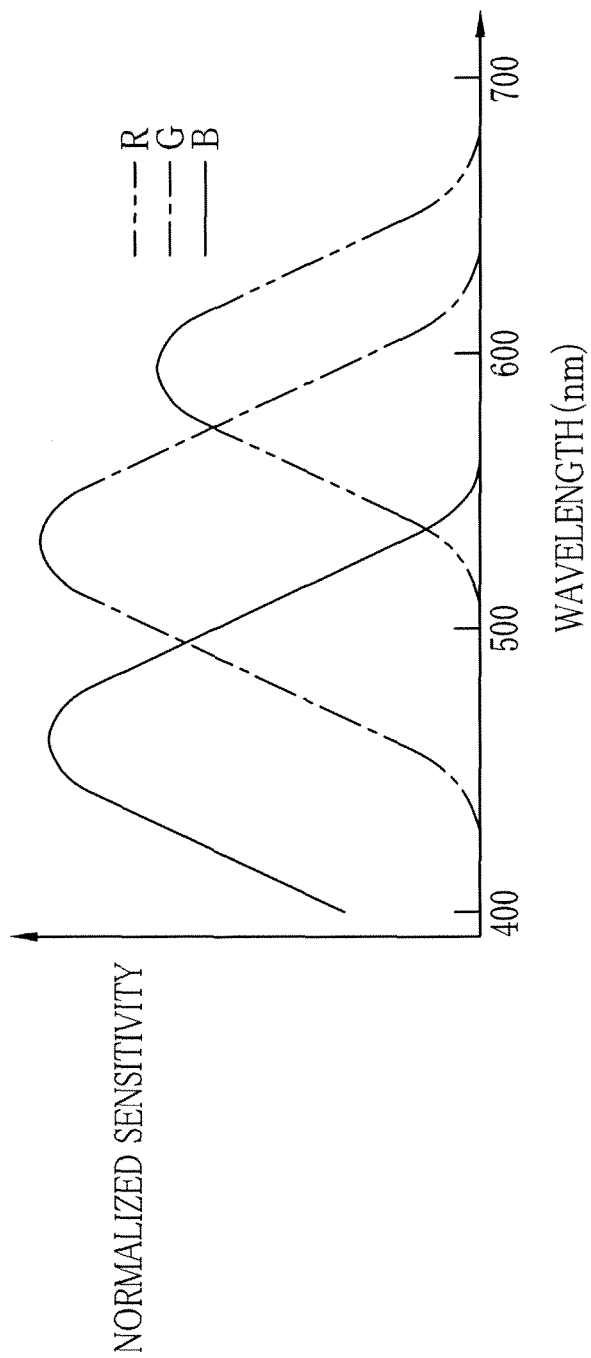
FIG. 4 is a graph showing spectral sensitivity of a CCD.

The CCD 35 is positioned such that the objective lens system 34 forms an optical image of the target site on an imaging surface of the CCD 35. The imaging surface has a color filter formed thereon. The color filter may for example consist of primary-color (RGB) filter segments arrayed in the Bayer arrangement. According to spectral transmittances of the color filter and basic spectral sensitivity of sensor pixels of the CCD 35, the CCD 35 will show such spectral sensitivity characteristics with respect to the primary three color light components as shown in FIG. 4. That is, the red (R) pixels are sensitive to light of around 650 nm, the green (G) pixels to light of around 550 nm, and the blue (B) pixels to light of around 450 nm in wavelength.

The handling portion 14 is provided with an analog signal processing circuit (AFE) 38, a CCD drive circuit 39, and a CPU 40. The AFE 38 includes a correlated double sampling circuit (CDS), an automatic gain control circuit (AGC), and an analog-to-digital converter (A/D), through these are omitted from the drawings. The CDS subjects the image signal from the CCD 35 to the correlated double sampling process, reducing reset noises and amplification noises from the image signal. The AGC amplifies the noise-reduced image signal at a gain or amplification rate that is designated by the processor unit 11. The A/D converts the amplified image signal to a digital signal of a given bit number. The digitalized image signal is fed to an image processing circuit 49 of the processor unit 11 through the transmission cable.

The CCD drive circuit 39 generates drive pulses to the CCD 35, including pulses for vertical and horizontal scanning, electronic shutter pulses, reading pulses and reset pulses, as well as synchronizing pulses for the AFE 38. The CCD 35 acquires the image signal in response to the drive pulses from the CCD drive circuit 39. The components of the AFE 38 operate on the basis of the synchronizing pulses from the CCD drive circuit 39.

The CPU 40 of the endoscope 10 activates the CCD drive circuit 39 upon an operation start command from the CPU 45 of the processor unit 11 after the endoscope 10 is connected to the processor unit 11. The CPU 40 controls the gain at the AGC 38 through the CCD drive circuit 39.

The CPU 45 controls the overall operation of the processor unit 11 comprehensively. The CPU 45 is connected to the respective components of the processor unit 11 via not-shown data buses, address buses and control lines. ROM 46 stores various programs (OS, application programs etc.) and data (graphic data etc.) for use in controlling the operation of the processor unit 11. The CPU 45 reads out the program or data from the ROM 46 according to the need, and develops the read program or data in a RAM 47, a work memory, to execute the read program sequentially. The CPU 45 also obtains information about each individual examination, such as the date and time of examination, and text data about the patient and the surgeon, from an operating section 48 of the processor unit 11 or a network like LAN (local area network). The obtained information is stored in the RAM 47.

The operating section 48 includes an operation panel mounted on a housing of the processor unit 11 or well-known input devices such as a mouse and a keyboard. The CPU 45 controls the respective components of the processor unit 11 according to operation signals from the operating section 48 and the handling portion 14 of the endoscope 10, including the release button and the mode change-over switch 20.

The image processing circuit 49 processes the image signal from the endoscope 10 for various kinds of image processing, such as color compensation, white balance adjustment, gamma correction, image enhancement, image noise reduction, color conversion, etc. As set forth in detail later, the image processing circuit 49 also makes a process for eliminating those spectral components from the image signal which are originated from extraneous objects that are out of diagnostic interests. Bile may be one of such extraneous objects.

A display control circuit 50 receives graphic data from the CPU 45. The graphic data is read out from the ROM 46 and the RAM 47, and includes data of display masks for masking out ineffective image areas of the endoscopic image so as to display an effective image area alone, data of the examination date and time, data of text information about the patient and the operator, or the presently selected inspection mode, data for graphical use inter face (GUI), etc. The display control circuit 50 processes the image data from the image processing circuit 49 for superimposing the display mask, the text information, or the GUI onto the endoscopic image, and controls displaying the endoscopic image on the monitor 19.

The display control circuit 50 has a not-shown frame memory for temporary storage of the image data. The display control circuit 50 reads out the image data from the frame memory to convert the image data to a video signal compatible to the display format of the monitor 19, such as a component signal or a composite signal. Thus the endoscopic image is displayed on the monitor 19.

Beside the above components, the processor unit 11 is provided with a data compressing circuit for compressing the image into data of a predetermined format, e.g. JPEG format, a media interface for recording the compressed image on removable media such as CF card, optical magnetic disc (MO), CD-R, etc., and a network interface for controlling data transmission between the system 2 and the network such as LAN. These components are connected to the CPU 45 via data bus or the like.

The light source unit 12 has an ordinary inspection light source 60 and a special inspection light source 61. These light sources 60 and 61 may have the same structure and may be a xenon lamp, a halogen lamp or a white LED (light emission diode) each, which emits white light having even intensity across a broad wavelength band ranging from blue to red, e.g. from 400 nm to 750 nm. The light source 60 or 61 may also be one that produces white light as composite light composed of blue or ultraviolet exciting light and fluorescence of green to yellow to red that is emitted from a phosphor as excited by the exciting light. Alternatively, the special inspection light source 61 may be constituted of multiple semiconductor diodes or LEDs, which emit narrowband rays of different wavelength bands.

The light sources 60 and 61 are driven by light source drivers 62 and 63, respectively. Condenser lenses 64 and 65 collect light beams from the light sources 60 and 61 to introduce the collected beams into light guides 36a and 36b, which are provided at the outputs of the light sources 60 and 61, respectively. The light guides 36a and 36b are coupled into a light guide 36 within the light source unit 12 using a well-known optical fiber coupling technique. A movable stop member 66 or 67 is mounted between the condenser lens 64 or 65 and the light guide 36a or 36b, respectively. The light guide 36, the projection lens 37, the condenser lenses 64 and 65, and the movable stop members 66 and 67 constitute an illuminating optical system. In an alternative, light guides may be provided separately for the respective light sources 60 and 61, instead of the branched light guides 36a and 36b.

A wavelength tunable element 68 is provided between the light source 61 and the condenser lens 65. The wavelength tunable element 68 is driven by an element driver 69. The wavelength tunable element 68 selectively transmits rays of a limited wavelength band among incident light, wherein the transmittable wavelength band or pass-band is tunable. The light source unit 12 has a CPU 70 that may communicate with the CPU 45 of the processor unit 11, to control the operation of the light source drivers 62 and 63, the movable stop members 66 and 67, and the element driver 69.

The wavelength tunable element 68 may be an etalon, a liquid crystal tunable filter or a rotary filter fabricated by combining several interference filters (band-pass filters). The etalon controls the transmitting wavelength band or pass-band by driving an actuator such as a piezoelectric element to change the interplanar distance of a substrate consisting of a couple of highly reflective light filters. The liquid crystal tunable filter is fabricated by sandwiching a birefringent filter and a nematic liquid crystal cell between polarizing filters and controls the pass-band by changing voltage levels applied to the liquid crystal cell.

In the ordinary inspection mode, the CPU 45 controls the light source driver 62 via the CPU 70, to turn on the light source 60 alone. Thus, only the white light is projected as the illumination light toward the target site. When the special inspection mode is selected, the CPU 45 turns the light source 60 off and the light source 61 on. Thus, only the narrowband light that has passed through the wavelength tunable element 68 is projected toward the target site.

The special inspection mode is to acquire information about blood vessels in the target site, wherein the wavelength tunable element 68 is controlled to transmit rays in given narrow wavelength bands and the CCD 35 captures the image of the target site from the narrowband rays reflected from the target site. The projected narrowband ray may include, for example, those having center wavelengths of 405 nm, 445 nm and 473 nm which are suitable for measuring oxygen saturation of hemoglobin in superficial blood vessels, or those having center wavelengths of 680 nm, 805 nm and 950 nm which are suitable for measuring oxygen saturation of hemoglobin in deep blood vessels. Alternatively, narrowband rays having center wavelengths of 450 nm, 550 nm and 780 nm may be projected in the special inspection mode, in order to acquire images of superficial-, intermediate- and deep-layer blood vessels respectively, i.e., the images visualizing blood streams.

Figure 5:
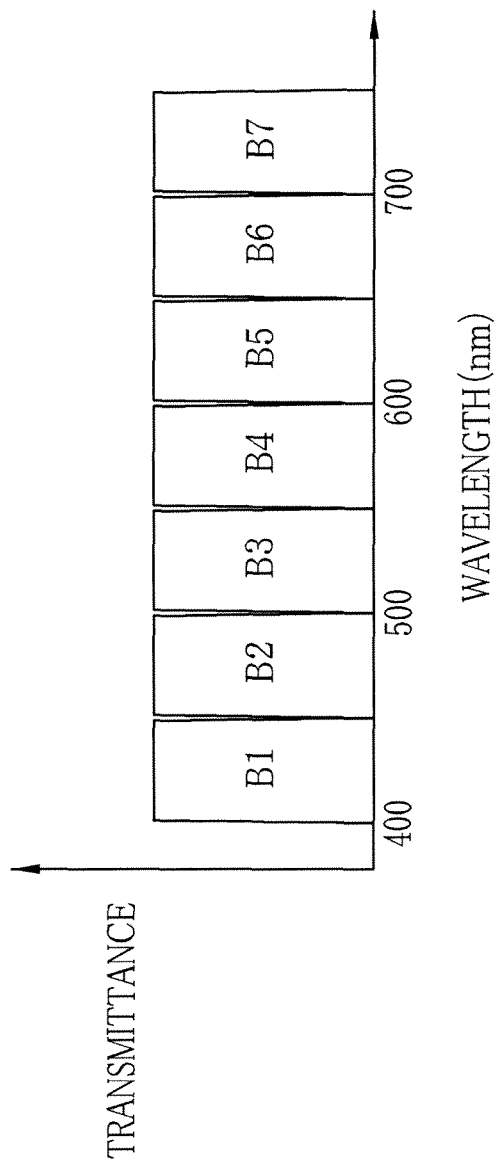
FIG. 5 is a graph showing spectral characteristics of a narrowband ray (spectral transmittance thereof through a wavelength tunable element), which is projected to acquire reflection spectra.

In addition to the narrowband rays for acquiring vascular information, narrowband rays of multiple wavelength bands are projected toward the target site, and the CCD 35 captures an image of the target site from each of these narrowband rays as reflected from the target site, thereby to obtain spectral data of the rays reflected from the target site, hereinafter referred to simply as the reflection spectra. As shown for example in FIG. 5, the wavelength tunable element 68 is driven to sequentially select one of transmission wavelength bands B1 to B7 having a width of 50 nm each, which are defined by diving a wavelength range of 400 nm to 750 nm into the seven 50 nm-bands. These bands B1 to B7 are switched over synchronously with the charge-accumulation interval of the CCD 35. The reflection spectra may be obtained upon the system being switched to the special inspection mode or upon an instruction entered through the operating section 48 by the operator.

Figure 6:
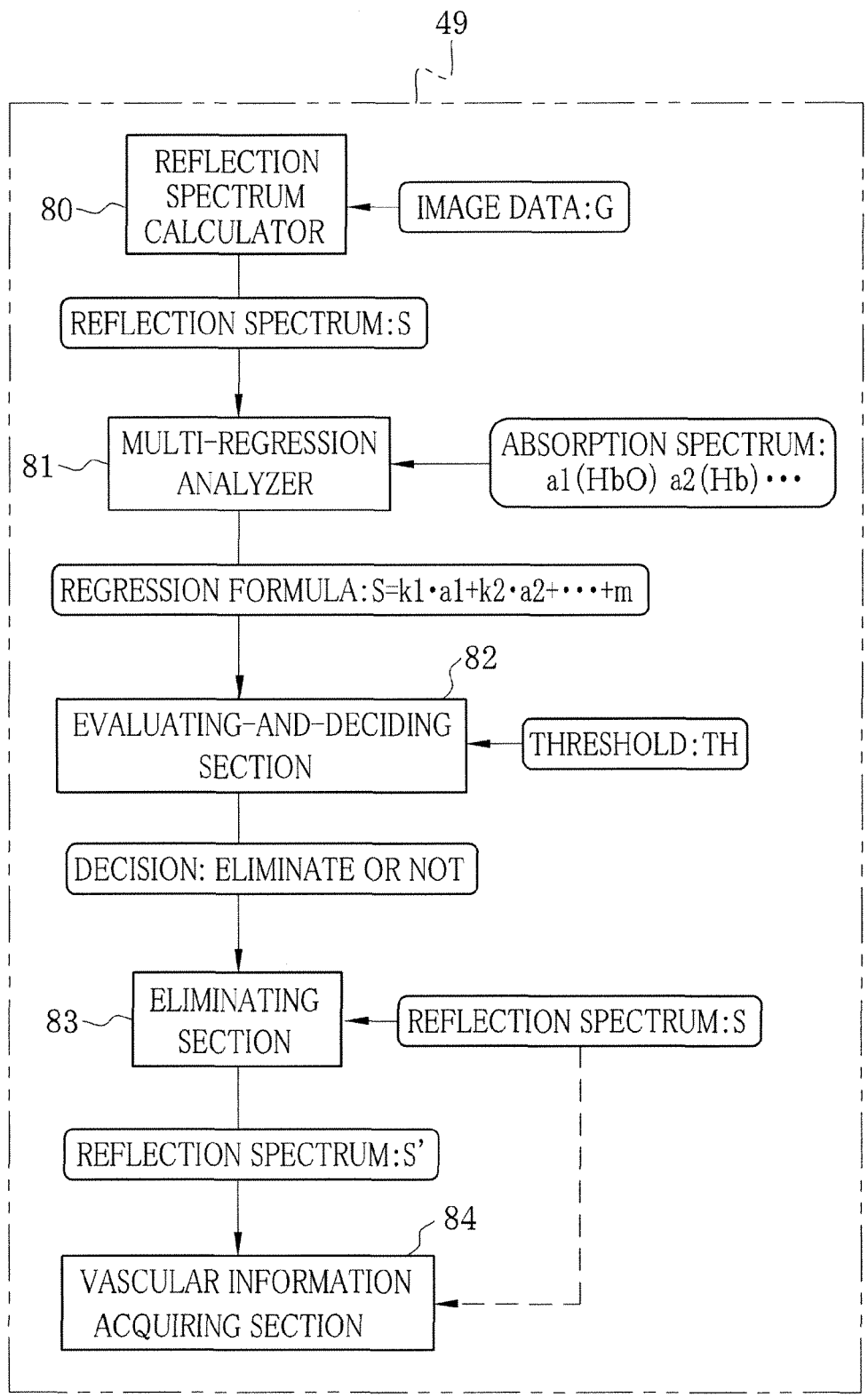
FIG. 6 is a block diagram illustrating details of an image processing circuit.

In an embodiment of FIG. 6, the image processing circuit 49 is provided with a reflection spectrum calculator 80, a multi-regression analyzer (corresponding to the claimed contribution calculator) 81, an evaluating and deciding section 82, an eliminating section (corresponding to the irrelevant object eliminator) 83, and a vascular information acquiring section 84.

The reflection spectrum calculator 80 obtains the reflection spectra S on the basis of image data G of a number of frames that the CCD 35 captures while the narrowband rays for acquiring vascular information and the narrowband rays in the bands B1 to B7 are sequentially projected toward the target site. Pixel levels of this image data G represent intensities of the narrowband rays reflected from the target site in the wavelength bands for acquiring vascular information as well as in the wavelength bands B1 to B7. Therefore, the pixel levels of the image data may be applied to calculating the spectral intensities of the reflected rays in the respective wavelength bands, providing reflection spectra S across the wavelength range of 400 nm to 750 nm.

Because the sensitivities of the RGB pixels of the CCD 35 and the intensity of the white light from the special inspection light source 61 vary depending on the wavelength band, it is necessary to compensate for the sensitivity variations and intensity variations with the wavelength bands when substituting the pixel levels of the image data G for the intensities of the reflection spectra S. In an embodiment, correction coefficients for this compensation are previously memorized in the ROM 46. The correction coefficients are predetermined for the respective narrow wavelength bands, including those used for acquiring vascular information and the bands B1 to B7, according to the sensitivity variations of the RGB pixels of the CCD 35 and the intensity variations of the white light from the special inspection light source 61. The pixel levels of the image data G are normalized by multiplying by the predetermined correction coefficients before being applied to the calculation of the reflection spectra S, thereby to cancel those differences between the pixel levels which are resulted from the sensitivity variations of the CCD pixels and the intensity variations of the white light with the wavelength. For example, normalizing the maximum sensitivity of the CCD 35 as "1", when the CCD 38 has a sensitivity of "0.8" to the rays in the bands B1, pixel levels of the image data G acquired from the rays in the bands B1 are multiplied by 1/0.8=1.25.

In an embodiment, the pixel levels applied to the calculation of the intensities of the reflection spectra S are predetermined for each wavelength band: an average level of blue pixels of the image data G acquired from the rays in the band B1, i.e. blue ray band, is substituted for the intensity of the blue region of the reflection spectra S, and an average level of red pixels of the image data G acquired from the rays in the band B7, i.e. red ray band, is substituted for the intensity of the red region of the reflection spectra S.

It is possible to apply respective RGB pixel levels to the spectral intensity calculation, so that at once three kinds of intensity values for the reflection spectra S may be obtained from each of the sequentially projected narrowband rays. Spectrally dividing the illumination light into different wavelength bands and then receiving the light on the CCD 35 after spectrally dividing it through color filters will lead to getting information about many reflection spectra S in a small number of frames.

Figures 7, 8:
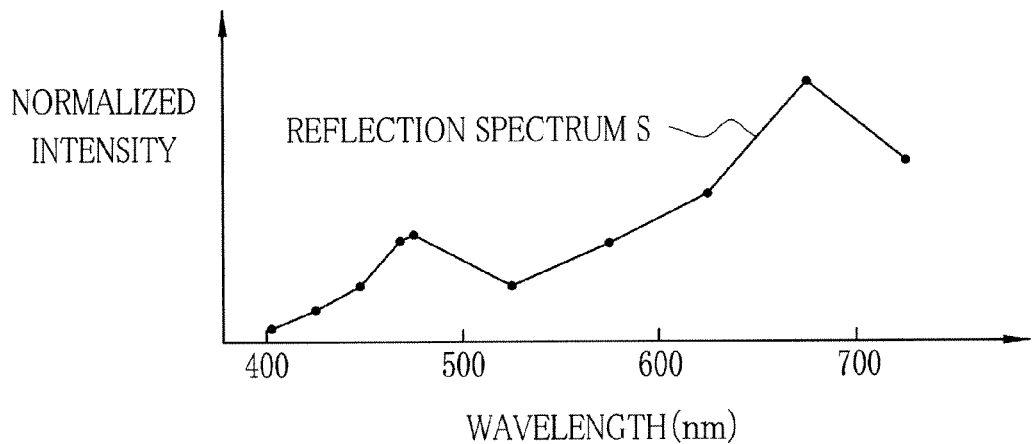
FIG. 7 is a graph showing the reflection spectra.
FIG. 8 is a diagram showing data of absorption spectra of various objects as stored in a data table.

An example of the reflection spectra S obtained by the reflection spectrum calculator 80 may be plotted on a line graph as shown in FIG. 7, wherein the spectral intensities determined by the pixel levels are plotted at the center wavelengths of the respective wavelength bands for acquiring vascular information, at 405 nm, 445 nm and 473 nm in this example, and at the center wavelengths of the respective bands B1 to B7, i.e. at 425 nm, 475 nm, 525 nm, 575 nm, 625 nm, 675 nm and 725 nm. The reflection spectrum calculator 80 outputs the data of the obtained reflection spectra S to the multi-regression analyzer 81.

The reflection spectrum calculator 80 may calculate the reflection spectra S with respect to those parts of the image which correspond to blood vessels. The parts corresponding to blood vessels may for example be identified by the difference in luminance between pixels because the blood vessels have different luminance values from other parts. Alternatively, the reflection spectrum calculator 80 may also calculate the reflection spectra S with respect to a region of interest (ROI) that the operator can designate within the acquired image by operating the operating section 48. It is also possible to calculate the reflection spectra S for each individual subdivided segment of the imaging area of the CCD 35. The same applies to the following stages, including the multi-regression analyzer 81 and the vascular information acquiring section 84.

The multi-regression analyzer 81 makes multi-regression analysis using the reflection spectra S as a response variable, and absorption spectra a1, a2 . . . of blood and bile as explanatory variables. Since the reflection spectra S cover the whole wavelength range of the light reflected from the target site, ranging from 400 nm to 750 nm, it can be regarded as a sum of absorption spectra of multiple objects existing in the target site and absorbing light in the wavelength range of 400 nm to 750 nm, as being multiplied by appropriate coefficients. Concretely, the reflection spectra S may be expressed by the following equation (hereinafter referred to as the regression formula:

$$S = k1 \cdot a1 + k2 \cdot a2 + \ldots + m = \Sigma kn \cdot an + m$$

wherein k1, k2 . . . and m represent weighting coefficients, and n represents a natural number.

In the multi-regression analysis, these weighting coefficients are determined through the least-squares method or the like. More specifically, these weighting coefficients are determined by solving a system of equations, in which a root-mean-square difference between a reflection spectrum S obtained by the reflection spectrum calculator 80 (an actual measurement value) and a reflection spectrum S obtained through the regression formula (a calculus value) is set to zero by differentiation with respect to the weighting coefficients, so as to minimize the root-mean-square difference between the actual measurement value and the calculus value. The multi-regression analyzer 81 outputs data of the regression formula, including the determined weighting coefficients, to the evaluating and deciding section 82. It should be noted that the absorption spectra have inverted intensities to the reflection spectra, and hence they represent substantially the same optical property. Therefore the above formula, by which the absorption spectra of the respective objects are multiplied by the weighting coefficients and summed up, may stand for the regression formula of the reflection spectra S.

The absorption spectra a1, a2 . . . of those objects which potentially exist in the target site may be previously memorized in the ROM 46, in the form of an absorption spectrum table 90 as shown in FIG. 8. The absorption spectrum table 90 stores data of absorption spectra of individual objects, each in association with the substance name and its identifier a1, a2 . . . used in the regression formula. The absorption spectra may be linear data plotted on a line graph in the same manner as the reflection spectra S shown in FIG. 7.

Specifically, the identifiers a1 and a2 respectively represent the absorption spectra of oxygen hemoglobin (HbO) and reduced hemoglobin (Hb), whereas a3 represents the absorption spectra of blood, a4 blood plasma, and a5 bile. The identifiers a9, a10 and a11 represent the respective absorption spectra of indigocarmine, crystal violet and iodine, which may be administered into the test subject for staining the target site. Note that the absorption spectra data may be non-linear data, or data of a combination of absorption spectra of various objects. The absorption spectra data may also include DC components. The absorption spectrum table 90 may be recorded on a removable medium instead of the ROM 46, so that it may be read out from the removable medium into the image processing circuit 49.

Based on the data of regression formula from the multi-regression analyzer 81, the evaluating and deciding section 82 evaluates the degree of contribution of irrelevant objects, or objects of no interest, to the reflection spectra S, and decides by the evaluation result whether the eliminating section 83 should eliminate spectral components originated from the objects of no interest from the reflection spectra S. The objects of no interest include such substances that may hinder the acquisition of the vascular information, while blood or its components like oxygen hemoglobin and reduced hemoglobin are relevant objects necessary for acquiring vascular information. In the present embodiment, secretions such as bile and mucin, and staining materials such as indigocarmine are recited as the objects of no interest.

The evaluating and deciding section 82 compares the weighting coefficient assigned to the absorption spectra of irrelevant objects in the regression formula, e.g. the weighting coefficient k5 when bile is the irrelevant object, with a predetermined threshold TH. If the compared weighting coefficient is greater than the threshold TH, the evaluating and deciding section 82 evaluates that the contribution degree of the irrelevant object to the reflection spectra S is high, and decides that spectral components originated from the irrelevant objects should be eliminated from the reflection spectra S in the eliminating section 83. On the other hand, if the weighting coefficient is not greater than the threshold TH, the evaluating and deciding section 82 evaluates that the contribution degree of the irrelevant object is so low that this irrelevant object does not affect the acquisition of the vascular information, and decides not to eliminate the spectral components of the irrelevant object from the reflection spectra S. Then the evaluating and deciding section 82 outputs the decision to the eliminating section 83.

The evaluating and deciding section 82 may make the evaluation and decision in other ways. For example, the evaluation and decision may be made depending upon the result of comparison of the difference or ratio between the weighting coefficient for the irrelevant object and the weighting coefficient for the relevant object with a threshold. If the difference or ratio between the compared weighting coefficients is greater than the threshold, the evaluating and deciding section 82 decides to eliminate the spectral components of the irrelevant object. Alternatively, a value calculated from multiple weighting coefficients, e.g. a weighted average of the respective weighting coefficients may be used as an index for the evaluation and decision.

The evaluation and decision may also be made on the basis of statistics for judging significance of the regression formula obtained by the multi-regression analysis or the weighting coefficients of this formula. The applicable statistics may include p-value, F-value and a degree-of-freedom adjusted coefficient of determination (contribution rate or degree of influence). The p-value indicates reliability of the weighting coefficients such that the weighting coefficients determined by the multi-regression analysis may be more reliable and true the closer the p-value to zero. The F-value is served as an index for statistical hypothesis testing as to whether to withdraw a null hypothesis that the regression formula is not useful for calculating the reflection spectra S, and adopt an alternative hypothesis that the regression formula is useful for calculating the reflection spectra S. The degree-of-freedom adjusted coefficient of determination is an index indicating how much degrees the absorption spectra a1, a2 . . . in total, explanatory variables, can forecast the reflection spectra S as an objective variable. Based on these statistics, the evaluating and deciding section 82 may judge the significance of the regression formula and the significance of the weighting coefficient for the irrelevant object. Then, the evaluating and deciding section 82 may decide to eliminate the spectral components of irrelevant objects when the regression formula and the weighting coefficient for the irrelevant object are judged to be significant and, at the same time, the weighting coefficient for the irrelevant object (or the difference of the weighting coefficient for the irrelevant object from the weighting coefficient for the relevant object, or the ratio between them) is greater than the predetermined threshold TH. Alternatively, the decision may be made upon the significance judgment alone, without making the comparison with threshold TH.

When the decision of the evaluating and deciding section 82 is "to eliminate", the eliminating section 83 eliminates the spectral components originated from irrelevant objects (the fractions that the irrelevant objects contribute to or have influence on the reflection spectra S) from the reflection spectra S, for example, by subtracting those data values which are produced by multiplying the absorption spectra of the relevant objects by the weighting coefficients from the actual measurement values of the reflection spectra S. Then the eliminating section 83 outputs the reflection spectra S' from which the spectral components of irrelevant objects are eliminated, hereinafter referred to as the subsequent reflection spectra S', to the vascular information acquiring section 84. On the other hand, when the decision of the evaluating and deciding section 82 is "not to eliminate", the eliminating section 83 is not activated, and merely the reflection spectra S obtained by the reflection spectrum calculator 80 is transferred to the vascular information acquiring section 84.

The vascular information acquiring section 84 acquires information about blood vessels in the target site on the basis of the reflection spectra S and/or the subsequent reflection spectra S': using both reflection spectra S and S' when decided to eliminate the components of irrelevant objects, or using only the reflection spectra S when decided not to eliminate. The vascular information may include oxygen saturation of blood hemoglobin, images of superficial, intermediate and deep blood vessels, and depths of the vessels from the surface of the target site. For example, in order to acquire information about oxygen saturation, the vascular information acquiring section 84 calculates intensity ratios between the intensities of the reflection spectra S or the subsequent reflection spectra S', for example, at the wavelengths of 405 nm, 445 nm and 473 nm, and derives oxygen saturation values corresponding to calculated intensity ratios from a predetermined relation between the intensity ratio and the oxygen saturation. The vascular information acquiring section 84 may also acquire the vessel depth information from the intensities of the reflection spectra S or the subsequent reflection spectra S', for example, at the wavelengths of 450 nm, 550 nm and 780 nm. That is, if the spectral intensity at 450 nm is higher than others, it may represent superficial blood vessels, whereas high intensity at 550 nm may represent intermediate blood vessels, and high intensity at 780 nm may represent deep blood vessels.

In order to acquire an image visualizing the blood streams, as another kind of the vascular information, the eliminating section 83 takes a reversed procedure to that taken by the reflection spectrum calculator 80 to obtain the reflection spectra S from the pixel levels: multiplying the absorption spectra of irrelevant objects with weighting coefficients, converting the multiplication products to pixel levels, and subtracting these pixel levels from the image data. Alternatively, the oxygen saturation or the vessel depth information may be obtained from data of pixel-level-subtracted images. Specifically, the oxygen saturation or the vessel depth may be calculated from luminance ratios between those pixel-level-subtracted images which are obtained under the narrowband rays of above-mentioned wavelengths. The oxygen saturation or the vessel depth may also be calculated from the amounts of blurs in these images.

Figure 9A:
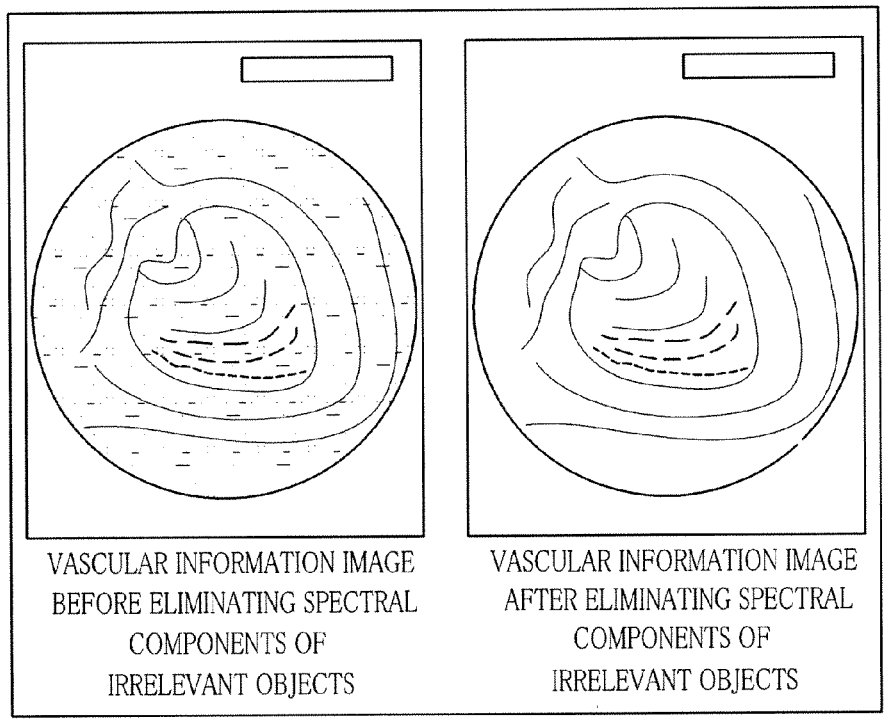
FIG. 9A is a diagram illustrating an example of display for images with blood information.

The vascular information acquired by the vascular information acquiring section 84 is overlaid on a composite image that may consist of multiple frames of image data G or the like, to be displayed as a vascular information image on the monitor 19. The display control circuit 50 may control the monitor 19 to display the vascular information image obtained based on the reflection spectra S and the vascular information image obtained based on the subsequent reflection spectra S' one by one. The vascular information image based on the reflection spectra S and the vascular information image based on the subsequent reflection spectra S' may also be displayed side by side, as shown in FIG. 9A. The way of displaying these vascular information images may be switched over in response to a manual operation or automatically at regular time intervals. Instead of the side-by-side display, these images may be displayed in an overlaid fashion. This facilitates comparison between these images, and hence the diagnoses. Moreover, the operator can visually confirm the function of the eliminating section 83, and feel more assured. If the evaluating and deciding section 82 decides that there is no need for the elimination, the monitor 19 will display only the vascular information image obtained based on the reflection spectra S without the elimination process.

The vascular information may be displayed as numerical values or text. For example, the oxygen saturation may be indicated as numerical values (%), and the vessel depth may be indicated as annotations such as "superficial", "intermediate", etc. to the corresponding vessels. Alternatively, the vascular information may be expressed as color maps. For example, the vessels of low oxygen saturation may be displayed in cyan, the vessels of middle oxygen saturation may be displayed in magenta, and the vessels of high oxygen saturation may be displayed in yellow. Likewise, the superficial vessels may be displayed in blue, the intermediate vessels green, and the deep vessels red.

Figure 9B:
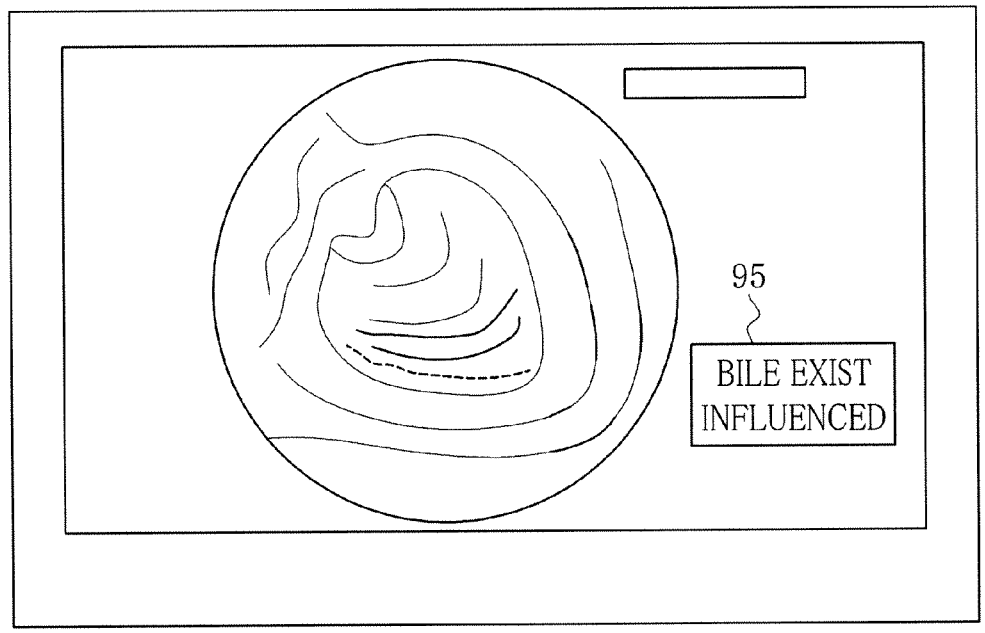
FIG. 9B is a diagram illustrating another example of display for an image with blood information.

After the reflection spectrum calculator 80 acquires the reflection spectra S and then the multi-regression analyzer 81 obtains the weighting coefficients of the regression formula, literal information 95 may be displayed in a way as shown for example in FIG. 9B, about whether any irrelevant objects are found or not, as well as whether the irrelevant objects have influence on the acquisition of the vascular information. Judgment as to whether any irrelevant objects exist or not and whether the irrelevant objects have any influence on the vascular information may be made with reference to the decision by the evaluating and deciding section 82. For example, when the evaluating and deciding section 82 evaluates that the weighting coefficient of any irrelevant object is significant, and the weighting coefficient of the irrelevant object (or the difference thereof from the weighting coefficient of the relevant object, or the ratio thereof to the weighting coefficient of the relevant object) is above the threshold TH, the displayed literal information notifies that the irrelevant object exists and it has influence on the vascular information. Even if the weighting coefficient has significance, if it is below the threshold TH, the literal information notifies that the irrelevant object exists but it has no influence on the vascular information. In another embodiment, the weighting coefficients of the irrelevant objects may be directly displayed. It is also possible to change the level of display according to the magnitude of the weighting coefficients. For example, the literal information 95 may be twinkled if any of the weighting coefficients is largely above the threshold TH.

Next the operation of the electronic endoscope system 2 configured as above will be described. To inspect the inside of the test subject by the endoscope 10, the operator connects the endoscope 10 to the respective units 11 and 12, and turns on the powers of the respective units 11 and 12. Then the operator operates the operating section 48 to input information about the test subject and other data before inputting a start command.

After inputting the start command, the operator introduces the probing portion 13 into the test subject while illuminating the inside of the subject body with the illumination light from the light source unit 12, and watching the images of internal organs of the test subject on the monitor 19, the inspection images captured by the CCD 35.

The image signal output from the CCD 35 is processed through the respective components of the AFE 38, and then fed to the image processing circuit 49 of the processor unit 11. In the image processing circuit 49, the input image signal is processed in various ways to produce an image. The image processed in the image processing circuit 49 is fed to the display control circuit 50. The display control circuit 50 executes various kinds of display control processing according the graphic data from the CPU 45. Thus the inspection images are displayed on the monitor 19.

The electronic endoscope system 2 may be switchable between the ordinary inspection mode and the special inspection mode according to the inspection object. While the probing portion 13 is being introduced into the test subject body, the ordinary inspection mode should be selected to project the white illumination light in order to inspect the images in a wide field of view. When a lesion is found to be examined in detail, the special inspection mode is selected to project a narrowband ray of a wavelength suitable for the inspection of that lesion. The operator can operate the release button to capture still images, or insert any necessary surgical tool through the tool channel of the endoscope 10, so that the operator can inject staining material into the lesion, cut it off, or apply medication to it.

In the ordinary inspection mode, the ordinary inspection light source 60 is turned on under the control of the CPU 45, to project the white light from the light projection window 31 toward a target site.

In the special inspection mode, the special inspection light source 61 is turned on. The white light from the special inspection light source 61 is incident on the wavelength tunable element 68, so that narrowband rays of a limited wavelength band are selectively output from the wavelength tunable element 68. The narrowband ray from the wavelength tunable element 68 is conducted through the light guide 36 to the distal end 17 of the endoscope 10, to be projected from the light projection window 31 toward the target site.

Figure 10:
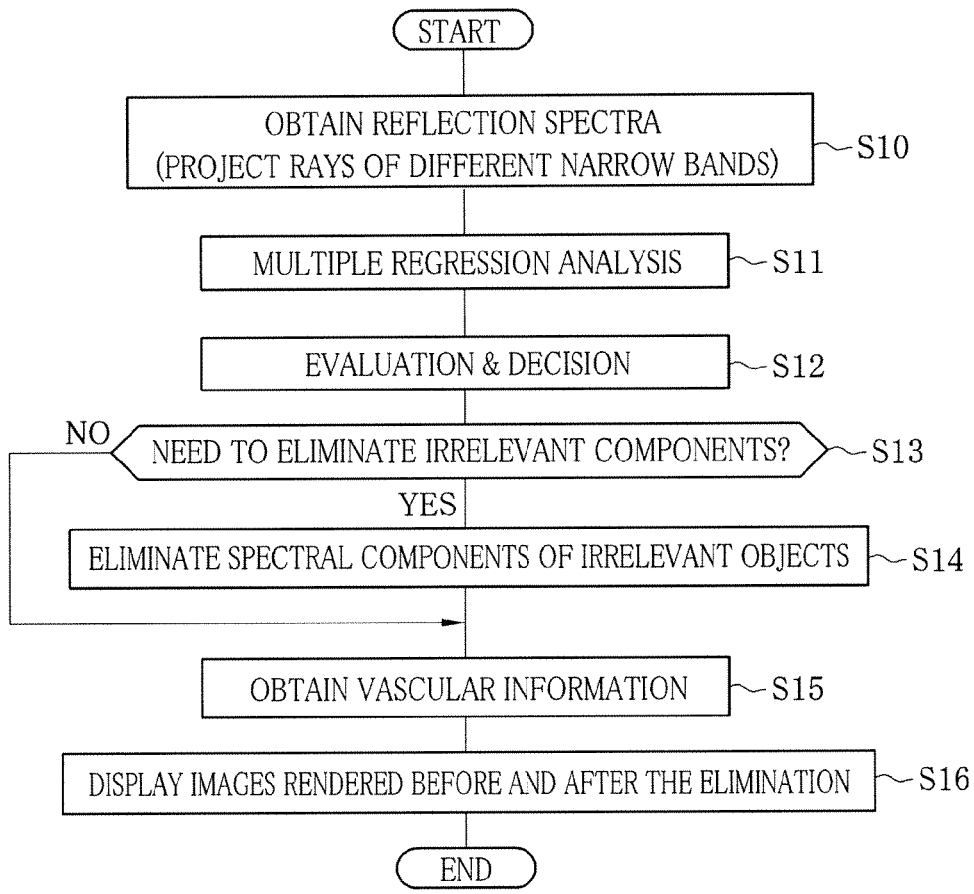
FIG. 10 is a flowchart illustrating a sequence of image processing.

In the special inspection mode, a reflection spectra acquiring process is executed, as shown in step 10 (S10) in FIG. 10. First, the wavelength tunable element 68 is driven to project the narrowband rays for acquiring vascular information and the narrowband rays of the bands B1 to B7, the seven 50 nm bands subdividing the wavelength range of 400 nm to 750 nm, toward the target site, turn by turn at the same intervals as the charge accumulation in the CCD 35. Thus, an image of the target site is captured by the CCD 35 each time the narrowband ray of one of these wavelength bands is projected. Thereby, multiple frames of image data G are obtained. Based on these multiple frame of mage data G, the reflection spectrum calculator 80 detects reflection spectra S.

After the reflection spectra S is thus obtained, the multi-regression analyzer 81 refers to the absorption spectrum table 90 to determine the regression formula representing the reflection spectra S using the respective absorption spectra "an" of the objects and the weighting coefficients "kn" and "m" thereof (S11). The evaluating and deciding section 82 compares the weighting coefficients of the irrelevant objects in the regression formula with the threshold TH, to decide whether the spectral components of the irrelevant objects should be eliminated from the reflection spectra S for use in acquiring the vascular information (S12).

When the result of judgment is "to eliminate" ("YES" in S13), the eliminating section 83 eliminates spectral components of the irrelevant objects from the reflection spectra S (S14). When the result is "not to eliminate" ("NO" in S13), the elimination of the spectral components of the irrelevant objects is not executed.

The vascular information acquiring section 84 acquires the vascular information on the basis of the reflection spectra S or the subsequent reflection spectra S' (S15). The acquired vascular information is processed in the display control circuit 50, for example, for false-coloring. The processed vascular information is displayed on the monitor 19 (S16). More specifically, when the result of judgment by the evaluating and deciding section 82 is "to eliminate", a vascular information image based on the reflection spectra S and a vascular information image based on the subsequent reflection spectra are displayed on the monitor 19, preferably in parallel to each other.

Since the vascular information is acquired after eliminating the spectral components of irrelevant objects from the reflection spectra, the vascular information becomes more reliable, so is the diagnosis based on the vascular information. Moreover, since it is determined whether the spectral components originated from the irrelevant objects have any influence on the vascular information, in order to skip the elimination process if the irrelevant objects have no remarkable influence on the acquisition of vascular information, the resource of the image processing circuit 49 would not be wasted by making the elimination process unnecessarily.

As the multi-regression analysis quantitatively provides the weighting coefficients representative of the magnitudes of the absorption spectra of irrelevant objects and the contribution degrees of the absorption spectra of irrelevant objects to the reflection spectra S, the weighting coefficients can be utilized for the following evaluation, decision and elimination processes.

Figure 11:
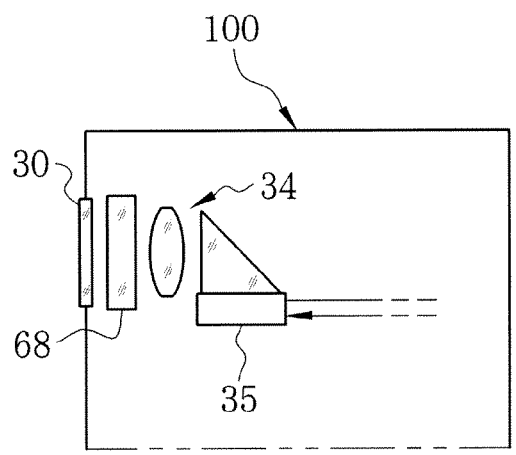
FIG. 11 is a diagram illustrating another embodiment wherein a wavelength tunable element is positioned in front of a CCD.

In the above embodiment, the wavelength tunable element 68 is disposed on the output of the special inspection light source 61. The wavelength tunable element 68 may be disposed on the output of the light guide 36. The wavelength tunable element 68 may also be disposed in the objective lens system for capturing images of the target site. For example, the wavelength tunable element 68 may be disposed behind an inspection window 30, as is shown in an endoscope 100 of FIG. 11, or may also be placed on the imaging surface of the CCD 35. In that case, the light source unit 12 shall have only an ordinary inspection light source, and the reflection spectra S will be obtained by changing the wavelength band of the incident light on the CCD 35 through the wavelength tunable element 68 while the white light is being projected from the ordinary inspection light source.

In the above embodiment, absorption spectra of various objects have been previously experimentally obtained. However, the respective absorption spectra of various objects may be measured as actual data during the inspection. In that case, the irrelevant objects are physically eliminated from the target site during the special inspection mode, in order to obtain image data G from the target site before and immediately after the physical elimination of irrelevant objects. Then, the reflection spectrum calculator 80 calculates the reflection spectra S and S" from the image data G obtained before and immediately after the elimination of irrelevant objects. The physical elimination of irrelevant objects may be done by blowing air or ejecting water into the body cavity of the test subject through the insufflating and watering nozzle 33 of the endoscope 10 or a specific tool inserted through the tool channel of the endoscope 10. Irrelevant objects may also be eliminated by suction into a catheter connected to an aspirator. Absorption spectra "an" of irrelevant objects will be obtained by subtracting the reflection spectra S" obtained after the elimination process from the reflection spectra S obtained before the elimination process. Therefore, in this embodiment, the absorption spectrum table 90 has only to memorize absorption spectra of relevant objects. The reason why the reflection spectra S" is obtained immediately after the physical elimination of the irrelevant objects is because some kinds of irrelevant objects like secretions, including bile, will come back to the same condition in a certain time after the physical elimination thereof. As for those irrelevant objects which are not secretions but staining materials, the difference between reflection spectra obtained before administration of the staining material (i.e. in a condition where the staining material does not exist in the target site) and reflection spectra obtained after the administration of the staining material (i.e. in a condition where the staining material exists in the target site).

The above-mentioned previously obtained absorption spectra of various objects may be representative examples, which do not take account of such differences in absorption spectra that may be resulted from individual variability of the test subjects or patients. According to the embodiment where absorption spectra of objects inside the patient are obtained as actually measured values in a real time fashion from differences between reflection spectra acquired before eliminating irrelevant objects and reflection spectra acquired after eliminating irrelevant objects, the differences between individual patients will be accommodated so that the subsequent vascular information will be more reliable.

Figure 12:
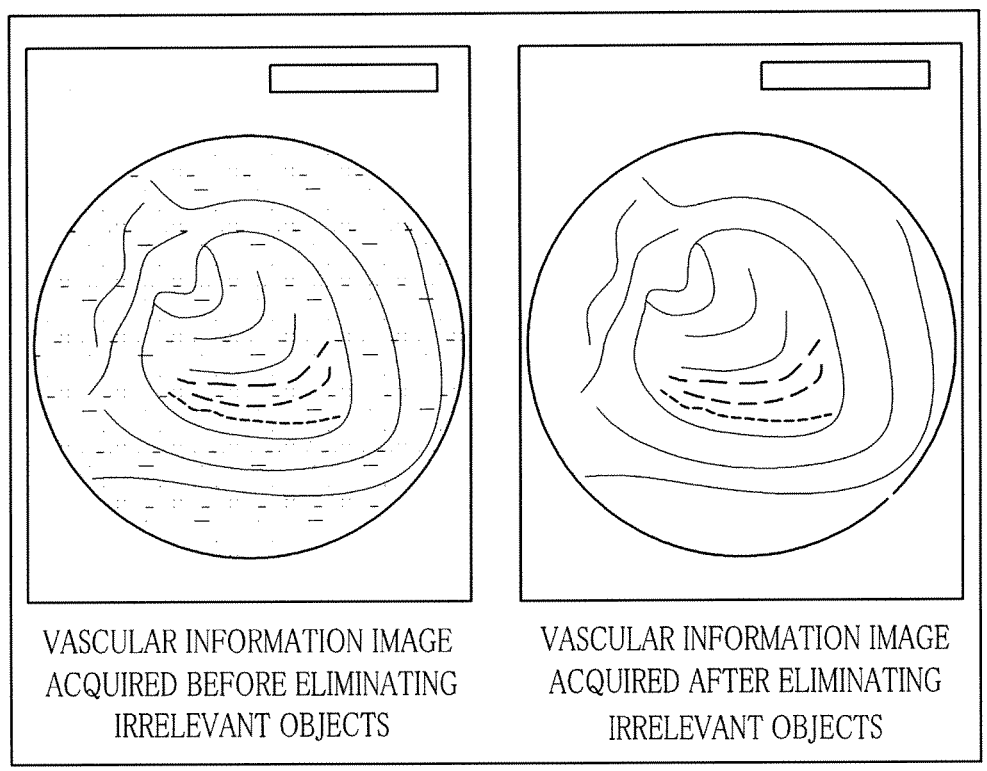
FIG. 12 is a diagram illustrating another example of display for images with blood information.

Also in the embodiment where the vascular information images are produced from image data acquired before and after eliminating irrelevant objects, the respective vascular information images may be displayed in parallel on the monitor 19, as shown in FIG. 12, or may also be displayed in an overlaid fashion (or in a time-sequential fashion if there is a time lag between the two conditions). It may also be possible to execute the elimination of spectral components originated from irrelevant objects in the eliminating section 83 in addition to the physical elimination of irrelevant objects, so as to display four vascular information images of the same target site: vascular information images produced before and after the spectral components of irrelevant objects being eliminated, and vascular information images acquired before and after irrelevant objects being eliminated, in parallel to each other or in a overlaid fashion. With reference to these images, the operator can see if the eliminating section 83 works well.

In the case where irrelevant objects are physically eliminated, the calculation of reflection spectra may be omitted, and the vascular information may be obtained based on the pixel levels using differences or ratios between weighting coefficients of irrelevant objects and weighting coefficients of relevant objects.

The real-time measurement of absorption spectra of the objects may be started in response to an operation on the 18 of the endoscope 10 or on an operational button of the specific tool for the physical elimination of irrelevant objects. It may also be preferable to make a database from absorption spectra of various objects, which have been obtained in the past.

In an alternative, discrimination between relevant objects and irrelevant objects may be selectable by the operator. For example, as shown in FIG. 13, a sorting list 105 may be displayed on the monitor 19, so that the operator can sort various substances into concerned, unconcerned and excluded objects by marking corresponding check boxes using the operating section 48. As for the excluded objects, items for absorption spectra of these substances are excluded from the regression formula, so that the multi-regression analysis of the excluded objects will not be executed.

The threshold TH for use in the evaluation and decision process may be adjustable by the operator using the operating section 48, or may also be automatically adjustable by the CPU 45.

The number of narrow wavelength bands in which the illumination light is time-sequentially projected for acquiring the reflection spectra S is not to be limited to the above embodiment but may be other than seven. Also the coverage of the illumination light is not to be limited to the range of 400 nm to 750 nm. The more the number of wavelength bands, the higher the resolution in calculating the reflection spectra S becomes, but it will take more time to acquire the reflection spectra S. Therefore, the number of wavelength bands should be determined appropriately so as to get an optimum balance between the resolution in calculating the reflection spectra S and the data acquisition time. Note that the narrowband rays for acquiring vascular information may not necessarily be projected if the resolution in calculating the reflection spectra S is sufficient.

The reflection spectra S may be obtained using other devices than the wavelength tunable element 68 as used in the above embodiment. For example, an optical image received from the target site may be spectrally divided through a color separation prism into multiple beams of different wavelength bands, to be captured by CCDs mounted on the respective outlet surfaces of the color separation prism. It may also be possible to use a spectrum analyzer that utilizes a digital light processor or DLP (a trade name), by OneLight Corporation (URL: http://www.onelightcorp.com/products/index.html), which adopts a xenon lamp as a light source and modifies the wavelength band of the light using an array of reflection mirrors in order to obtain reflection spectra of substances.

In the above embodiments, oxygen saturation and vessel depth are detected as information about the target site using the narrowband rays. However, the present invention should not be limited to the above embodiments. The present invention is applicable to those cases where a fluorescent material is injected into body tissues and then light for exciting the fluorescent material is projected toward a target site to inspect fluorescence from the target site, as well as where intrinsic fluorescence of body tissues is inspected.

It should be appreciated that the endoscope system relating to the present invention is not limited to the above embodiments, but various modifications may be possible without departing the scope and sprit of the present invention. For example, the imaging device is not limited to the above-described CCD image sensor, but may be a CMOS image sensor.

Although the CCD 35 is a primary-color CCD having RGB filters in the above embodiment, the endoscope system of the present invention may use a monochrome CCD. In that embodiment, a rotary filter is placed on the output side of an ordinary inspection light source or white light source. The rotary filter has RGB filters arranged around the circumferential direction, to transmit red, green and blue ray components of the white light according to the rotational position of the rotary filter. In the ordinary inspection mode, the three color rays are sequentially projected toward a target site, and the monochrome CCD captures image data of a corresponding color frame at each projection of one color light. Then a full-color image is produced from the three color image frames.

Furthermore, the present invention is applicable not only to an electronic endoscope system, but also to other kinds of endoscope systems, including those using an ultrasonic endoscope where an imaging device and an ultrasonic transducer are mounted in a scope distal end. The application field of the present invention is not limited to the medical field. The present invention may be applied to a system used in the industrial field. Accordingly, the above-mentioned objects of interest, or relevant objects, are not limited to blood or its components, and the information to be acquired by the endoscope system of the present invention is not limited to vascular or biological information.

What is claimed is:

1. An endoscope system comprising:
a light projecting device for projecting light toward a target site of a test subject for inspection;
an imaging device for capturing light reflected from or emitted from the target site to output an image signal;
a reflection spectrum obtaining device for obtaining first reflection spectra of the light projected from said light projecting device and reflected from the target site, the first reflection spectra having a wavelength range of 400 nm to 750 nm and being obtained by compensating pixel levels of image data of a plurality of frames obtained from said imaging device capturing narrowband rays in a plurality of bands according to sensitivity variations of pixels of said imaging device with the respective bands and applying the compensated pixel levels to calculating spectral intensities of the reflected light in the respective bands, said plurality of bands being defined by dividing the wavelength range of 400 nm to 750 nm;
a calculating device for calculating spectral components originated from irrelevant objects within the first reflection spectra through an analysis using the first reflection spectra as response variables and previously stored absorption spectra of the relevant and irrelevant objects as explanatory variables;
an eliminating device for eliminating the spectral components of the irrelevant objects as calculated by said calculating device from the first reflection spectra;
an information acquiring device for acquiring the information about the relevant object on the basis of the first reflection spectra and second reflection spectra from which the spectral components of the irrelevant objects have been eliminated; and
a display device for graphically displaying information about the relevant object, said display device concurrently or time-sequentially displaying the information about the relevant object in a condition before influence of the irrelevant objects is eliminated and in a condition after influence of the irrelevant objects is eliminated.

2. The endoscope system as recited in claim 1, wherein said reflection spectrum obtaining device obtains first reflection spectra in a condition where an irrelevant object exists in the target site and second reflection spectra in a condition where the irrelevant object does not exist in the target site, and determines the absorption spectra of the irrelevant object by subtracting the second reflection spectra from the first reflection spectra.

3. The endoscope system as recited in claim 1, wherein said calculating device carries out a multi-regression analysis using the first reflection spectra as response variables and the absorption spectra of the relevant and irrelevant objects as explanatory variables, and calculates the spectral components of the irrelevant objects by multiplying the absorption spectra of the irrelevant objects with respective weighting coefficients which are determined for each absorption spectrum by said multi-regression analysis.

4. The endoscope system as recited in claim 1, further comprising:
an evaluating and deciding device that evaluates the degree of influence of the individual irrelevant object on the first reflection spectra on the basis of the spectral component originated from the irrelevant object, to decide by the degree of influence whether to eliminate the spectral component of the irrelevant object from the first reflection spectra or not.

5. The endoscope system as recited in claim 4, wherein
said calculating device carries out a multi-regression analysis using the first reflection spectra as response variables and the absorption spectra of the relevant and irrelevant objects as explanatory variables, and calculates the spectral components of the irrelevant objects by multiplying the absorption spectra of irrelevant objects with weighting coefficients determined for the respective absorption spectra of irrelevant objects by said multi-regression analysis, and
said evaluating and deciding device evaluates the degree of influence of the irrelevant objects on the first reflection spectra using either the weighting coefficients determined for the absorption spectra of irrelevant objects by said multi-regression analysis or a statistic value for judging significance of said multi-regression analysis, or both.

6. The endoscope system as recited in claim 4, wherein said display device displays at least one of information as to whether there are any irrelevant objects in the target site, and the degree of influence of the irrelevant objects on the first reflection spectra.

7. The endoscope system as recited in claim 1, further comprising:
a sorting device for sorting between relevant and irrelevant objects in advance to the inspection.

8. The endoscope system as recited in claim 1, wherein the relevant object includes blood in blood vessels in the target site or at least a component of the blood, and
wherein the information acquiring device acquires information relating to the blood vessels.

9. The endoscope system as recited in claim 1, wherein the irrelevant objects include secretions from at least one of the test subject and staining materials applied to the test subject.

10. The endoscope system as recited in claim 1, wherein said light projecting device projects narrowband rays in said plurality of bands toward the target site.

11. The endoscope system as recited in claim 1, wherein said reflection spectrum obtaining device receives light reflected from the target site while spectrally dividing it into said plurality of bands.

12. The endoscope system as recited in claim 1, wherein said light projecting device projects broadband white light toward the target site, and
wherein said reflection spectrum obtaining device receives light reflected from the target site while spectrally dividing it into different wavelength bands.

13. The endoscope system as recited in claim 1, wherein said light projecting device or said reflection spectrum obtaining device includes a wavelength tunable element that is tunable in wavelength band of transmitting rays, and
wherein said wavelength tunable element is driven to sequentially select one of said plurality of bands as transmission wavelength bands.

14. The endoscope system as recited in claim 1, wherein said reflection spectrum obtaining device includes said imaging device, an objective lens system for forming an optical image of the target site on said imaging device, and a reflection spectrum calculator for calculating the reflection spectra based on the image signal output from said imaging device, and
wherein said objective lens system and said imaging device are disposed in a distal end of a probing portion of the endoscope.

15. A method of displaying images of a test subject inspected by an endoscope, said method comprising:
projecting light toward a target site of the test subject;
capturing light reflected from or emitted from the target site to output an image signal;
obtaining first reflection spectra of the light projected from said projecting and reflected from the target site, the first reflection spectra having a wavelength range of 400 nm to 750 nm and being obtained by compensating pixel levels of image data of a plurality of frames obtained from said capturing narrowband rays in a plurality of bands according to sensitivity variations of pixels of said imaging device with the respective bands and applying the compensated pixel levels to calculating spectral intensities of the reflected light in the respective bands, said plurality of bands being defined by dividing the wavelength range of 400 nm to 750 nm;
calculating spectral components originated from irrelevant objects within the first reflection spectra through an analysis using the first reflection spectra as response variables and previously stored absorption spectra of the relevant and irrelevant objects as explanatory variables;
eliminating the spectral components of the irrelevant objects as calculated by said calculating from the first reflection spectra;
acquiring the information about the relevant object on the basis of the first reflection spectra and second reflection spectra from which the spectral components of the irrelevant objects have been eliminated; and
graphically displaying information about the relevant object, said graphically displaying concurrently or time-sequentially displays the information about the relevant object in a condition before influence of the irrelevant objects is eliminated and in a condition after influence of the irrelevant objects is eliminated.

16. A method of displaying images of a test subject inspected by an endoscope, said method comprising:
projecting light toward a target site of the test subject;
capturing light reflected from or emitted from the target site to output an image signal;
obtaining first reflection spectra of the light projected from said projecting and reflected from the target site, the first reflection spectra having a wavelength range of 400 nm to 750 nm and being obtained by compensating pixel levels of image data of a plurality of frames obtained from said capturing narrowband rays in a plurality of bands according to sensitivity variations of pixels of said imaging device with the respective bands and applying the compensated pixel levels to calculating spectral intensities of the reflected light in the respective bands, said plurality of bands being defined by dividing the wavelength range of 400 nm to 750 nm;
calculating spectral components originated from irrelevant objects within the first reflection spectra through an analysis using the first reflection spectra as response variables and previously stored absorption spectra of the relevant and irrelevant objects as explanatory variables;
eliminating the spectral components of the irrelevant objects as calculated by said calculating from the target site;
acquiring the information about the relevant object on the basis of the first reflection spectra and second reflection spectra from which the spectral components of the irrelevant objects have been eliminated; and
graphically displaying information about the relevant object, said graphically displaying concurrently or time-sequentially displays the information about the relevant object in a condition before influence of the irrelevant objects is eliminated and in a condition after influence of the irrelevant objects is eliminated.

17. The endoscope system as recited in claim 1, wherein said eliminating device eliminates the spectral components of the irrelevant objects based on a predetermined threshold.

18. A method of displaying images as recited in claim 15, wherein said eliminating eliminates the spectral components of the irrelevant objects based on a predetermined threshold.

19. The endoscope system as recited in claim 1, wherein correction coefficients are previously memorized in a memory, said correction coefficients being predetermined for the respective bands according to sensitivity variations of pixels of said imaging device, and
   wherein said reflection spectrum obtaining device normalizes the pixel levels of the image data by multiplying the predetermined correction coefficients.

* * * * *